United States Patent [19]

Tulip

[11] Patent Number: 5,135,534
[45] Date of Patent: Aug. 4, 1992

[54] LASER LITHOTRIPSY

[76] Inventor: John Tulip, 11625 Edinboro Rd., Edmonton, Alberta, Canada, T6G 1Z7

[21] Appl. No.: 698,944

[22] Filed: May 13, 1991

Related U.S. Application Data

[62] Division of Ser. No. 506,446, Apr. 6, 1990.

[51] Int. Cl.$^5$ ............................................. A61B 17/22
[52] U.S. Cl. ............................ 606/178; 128/DIG. 28
[58] Field of Search ................................ 606/127, 128; 128/660.03, DIG. 28

[56] References Cited

U.S. PATENT DOCUMENTS 4,932,954  6/1990  Wondrazek et al. ............... 606/128

OTHER PUBLICATIONS

Nishioko, N. et al., "Mechanism of Laser-Induced Fragmentation of Urinary and Biling Colculi," Losers in the Life Sciences 1(3), 1987, pp. 231–245.

Primary Examiner—Kyle L. Howell
Assistant Examiner—Scott R. Akers
Attorney, Agent, or Firm—Andrus, Sceales, Starke & Sawall

[57] ABSTRACT

A laser lithotriptor includes a laser adapted to emit pulsed light which is absorbed by water in the vicinity of a human stone or concrement to cause rapid erosion of the stone. A light transmitting device such as a fibreoptic cable is employed inside of an endoscope to direct the laser pulses to the vicinity of the stones. An irrigation apparatus also ensures that the tip of the light transmitting device and the stone are continuously immersed in water and also serves to remove the powder-like debris of the disintegrated stone from the body. Preferably, a NdYAG laser operating at 1.44 μm which emits 27 pulses per second is coupled to the body stone through an anhydrous quartz fibreoptic cable passing through the interior of an endoscope.

5 Claims, 1 Drawing Sheet

LASER LITHOTRIPSY

This is a division of co-pending application Ser. No. 07/506,446 filed Apr. 6, 1990.

BACKGROUND AND SUMMARY OF THE INVENTION

The present invention relates to laser destruction of human calculi.

Lithotripsy, the crushing of human stones into easily removable fragments, is an old enterprise. Frere Jacques (of the French Folk song) was an itinerant lithotomist 300 years ago.

Modern medical practitioners, until recently, viewed gall bladder, kidney and ureteral stones as being removeable only by open surgery. Bladder stones, however, have been treated by endoscopic lithotripsy for many years. Physicians view the interior of the bladder with a cystoscope. This device is passed via the urethra into the bladder. An elongated lens combined with an eyepiece is passed along and attached to a sheath so that an image of the interior of the bladder may be seen. Typically, a cystoscope contains a means for passing irrigating fluid into and out of the bladder, a means for removing tissue samples from the bladder and a means of visualization.

Various methods of crushing bladder stones have been combined with the cystoscope: for example, mechanical crushing, mechanical drilling and more recently, ultrasonic disintegration.

The first ultrasonic lithotripsy of bladder stones occurred in Germany in 1968. The combined means of a cystoscope, a piezo-electric ultrasonic transducer and an interchangable ultrasonic probe was used. The probe is passed into the bladder under visual control. It will disintegrate some bladder stones on contact. Ultrasonic lithotriptors will not break hard stones. Each probe may be used for approximately 100 pulses before it must be replaced. Ultrasonic lithotriptors are consequently limited in use and expensive to operate.

The interior of the kidney (known as the pelvis of the kidney) may be visualized with the nephroscope, which is similar in use and appearance to the cystoscope. This endoscope is said to be used percutaneously where the sheath is passed into the kidney through the abdominal wall. Since the nephroscope became available, ultrasonic lithotripsy of kidney stones has become common practice. This practice is described, for example, by J. E. Lingeman in his article "Current concepts on the relative efficacy of percutaneous nephrostolithotomy and extracorporeal shockwave lithotripsy" in World Journal of Urology 5, 229, 1987, and by G. E. Brannen, W. H. Bush, R. E. Correa, R. P. Gibbons, and J. S. Elder in their article "Kidney Stone Removal, percutaneous versus surgical lithotomy" in Journal of Urology, 133, 6, 1985.

Approximately 50% of symptomatic urinary stone disease results from stones in the ureter. Ureteroscopes which may be either rigid or flexible are typically longer and thinner than other endoscopes. Ultrasonic lithotripsy is used very little in the ureter because of the rigid nature and relatively large diameter of the ultrasonic probe. See for example the article by J. L. Huffman, D. H. Bagley, H. W. Schoednberg and E. S. Lyon, "Transurethral removal of large ureteral and pelvic calculi using ureteroscopic ultrasonic lithotripsy" in the Journal of Urology, 130, 31, 1983.

Endoscopic destruction of gall stones has not become common medical practice although it is clearly possible.

The introduction in the early 1980's of the so called extracorporeal shockwave lithotriptor (E.S.W.L.) resulted in a significant improvement in the treatment of kidney stones. In this type of device a shock wave is created by an underwater high current spark discharge. By means of an elliptical acoustic reflector this shock wave is focused through the soft abdominal wall and kidney onto the kidney stone. The shock wave has little damaging effect on soft tissue but fractures hard stones. The resulting crushed stone is passed through the urinary tract. The E.S.W.L. is described, for example, by C. Chaussy, E. Schmiedt, D. Jocham, W. Brendel, B. Forsmann and V. Waltham in their article "First clinical experience with extracorporeally induced destruction of kidney stones by shock waves" in the Journal of Urology 127, 417, 1982 and more recently by G. W. Drach in "Report of the United States Cooperative Study of Extracoporeal shock wave lithotripsy, in the Journal of Urology, 135, 1127, 1986.

The E.S.W.L. is less effective for the treatment of ureteral stones. This is partly because of the difficulties in avoiding the pelvis and partly because ureteral stones are not immersed in liquid so that shock wave coupling to the stone is less efficient. For a discussion of this limitation of E.S.W.L. see the article by J. Graff, J. Pastor, P. Mach, W. Michel, P. J. Funhe, and T. Senge, "Extra corporeal shock wave Treatment of Ureteral Stones" in the Journal of Urology, 137, 143A, 1987.

The laser has recently been used as an alternative means for the destruction of ureteral stones. An extensive review is provided by the book entitled "Laser Lithotripsy" edited by R. Steiner, Springer Verlag, 1988. Typically the laser is focused into a fibre optic which is passed along a rigid or flexible ureteroscope. The ureteroscope is inserted through the bladder into the ureter and the stone is visualized. The operator may in this way direct intense pulses of light onto or in the vicinity of the stone and thus cause fracturing and disintegration of the stone. In the current state of the art as described by Steiner in "Laser Lithotripsy", two laser sources are effective in lithotripsy: the pulsed dye laser and the Q-switched NdYAG laser.

For a description of the operation of the pulsed dye laser, see the article by G. M. Watson, S. Murray, S. P. Dretley and J. A. Parrish in the Journal of Urology, 138, 195, 1987. Typically, pulses of visible light in the spectral region from 445 to 577 nm and of duration of 1 $\mu s$ to 300 $\mu s$ are used. The energy of each pulse is typically 10 mJ to 60 mJ. Typically the distal laser fibre tip touches the surface of a human stone which is immersed in water. A light pulse of sufficient intensity is then passed along the fibre. When a threshold of energy is exceeded a brilliant flash of light is emitted by the stone. This flash is accompanied by the disintegration of part of the stone. The white flash is accompanied by a clicking sound. The light emission by the stone and the shock which fractures the stone are attributed to the formation of a laser induced plasma. A discussion of this mechanism is in the paper by G. M. Watson.

Although the dye laser is reported to fragment all human calculi but the very hard uric acid and calcium oxalate monohydrate stones, it has several clinical shortcomings. The fragments of stone produced by dye laser lithotripsy tend to be relatively large compared with the powder produced by externally applied shock waves. Extraction of debris following lithotripsy is consequently a problem. If sharp debris is impacted in the ureter, for example, this represents a significant clinical problem.

Another difficulty encountered by users of dye laser lithotriptor is the variability of effectiveness. Formation of a plasma in a laser irradiated stone results from absorption of light by pigments in the stone. Pigmentation is variable. In renal stones it varies from almost white to dark brown. The laser conditions needed for formation of a plasma are difficulty to predict because the color of the stone is not known prior to lithotripsy. The size of fragments created by the dye laser is typically larger than fragments produced by a shock wave. The size of dye laser-produced fragments increases as the laser energy increases. Fragment size also increases as the depth of light penetration into the stone increases. Extraction of large fragments of stone from a ureter following dye laser lithotripsy is a significant clinical problem.

In an attempt to find a laser lithotriptor which does not depend upon the photochemical properties of human concrements, several groups have developed Q-switched NdYAG laser lithotriptors. See, for example, the article by F. Wondrazek and F. Frank, "Devices for intracorporal Laser induced Shock Wave Lithotripsy" in Laser Lithotripsy, Springer Verlag, 1988. Typically, in this type of device a 10 ns laser pulse from a Q-switched NdYAG laser with the wavelength of 1.06 $\mu$m is transmitted through a fibre from the laser to the vicinity of a stone. The stone is immersed in irrigating liquid which is typically water on saline and essentially transparent to the 1.06 $\mu$m laser light. Consequently, light emerging from the fibre will pass freely through the liquid and strike the stone or tissue in the vicinity of the stone and be absorbed. In the method of Q-switch NdYAG laser lithotripsy a small lens is attached to the output or distal end of the fibre so that light emerging from the fibre is focused a few millimeters from the said lens. If the intensity of laser light is sufficiently high a small plasma will form at the focus in a manner which is known as laser breakdown. The plasma absorbs light emerging from the fibre so that little light strikes the stone or tissue. The absorption results in a rapid deposition of energy into a small volume of plasma. The expansion of the hot plasma gases is limited by the surrounding liquid and an explosive increase in pressure results. The resulting shock wave radiates from the plasma in all directions at the speed of sound in the liquid. In the method of Q-switched laser lithotripsy a small parabolic reflecting surface is attached to the distal end of the fibre so as to reflect part of this shock wave toward a stone placed typically 3 mm from the plasma. Repeated impact of these shock waves on a stone tends to disintegrate the stone so that a lithotripic effect results. This method has the advantage that the photochemical composition of the stone does not influence the lithotripsy and the resulting stone fragments are similar to those produced by E.S.W.L. The disadvantages of this method are: the lens holding chamber is typically larger than two millimeters in diameter so that access to stones through a ureteroscope is limited; the larger rigid ureteroscope must be used; and the exposure of the lens to the plasma shock wave will destroy the lens after approximately 100 pulses. The limitations of this type of lithotripsy are discussed by S. Thomas, J. Pensel, W. Meyer and F. Wondrazeh in "The Development of an Endoscopically Applicable Optomechanical Coupler for Laser Induced Shock Wave Lithotripsy" in Laser Lithotripsy, Ed. R. Steiner, Springer Verlag, 1988.

In the present invention a method of laser lithotripsy uses laser light which is absorbed by water. Pulses of light absorbed by water in the vicinity of the stone cause erosion of the stone.

The geometry of the present laser lithotriptor includes a pulsed Neodymium Yttrium Aluminum Garnet, (NdYAG) laser operating at the wavelength 1.44 $\mu$m. This laser is described in the patent application number U.S. Ser. No. 06/933,10 filed by John Tulip in 1986. Unlike other emissions from the NdYAG laser, for example at the wavelengths of 1.06 $\mu$m and 1.32 $\mu$m, NdYAG laser emission at 1.44 $\mu$m is strongly absorbed by water. The depth over which this laser light is essentially absorbed by water is approximately 0.3 mm. Absorption of laser energy by water results in water heating and even vaporization if the laser light is sufficiently intense. In one example, this effect is used to vaporize human body tissue water with a focussed NdYAG 1.44 $\mu$m laser beam for surgical purposes. If the NdYAG laser is flashed or pulsed, the radiation may appear in intense, short bursts or pulses of energy. Such pulses of 1.44 $\mu$m radiation quickly heat and vaporize water.

Another part of this laser lithotriptor system is a quartz fibreoptic. Pulses of light from the said 1.44 $\mu$m NdYAG laser may be focussed into and along quartz fibreoptic. In particular quartz fibreoptic with very low OH content, commonly known as anhydrous quartz fibreoptic, effectively transmits 1.44 $\mu$m light. This fibreoptic may be used to direc laser pulses to the vicinity of body stones by passing the fibreoptic along such endoscopes as the ureteroscope.

Another part of this laser lithotriptor geometry is water in the vicinity and in contact with body stone. It is common practice to irrigate the bladder, ureter or kidney with water or water solutions such as saline during endoscopic examination. Natural body fluids are also composed largely of water. Therefore body stones are normally immersed in water.

We have discovered that a combination of these three means, applied correctly, will rapidly erode even the hardest calcium oxalate body stones.

It has been discovered that a microscopic explosion may occur at the distal, or output, tip of the fibreoptic when the fibre tip of the fibreoptic is placed in water and a pulse of 1.44 mm radiation is transmitted through the fibre. Apparently no plasma occurs in this explosion, no visible emission can be seen and no lens is placed at the fibre tip. The laser pulse period is typically up to tens of milliseconds which is much longer than the 10 nanosecond pulse period of the Q-switched 1.06 mm NdYAG laser. The velocity of sound in water is sufficiently high that a shockwave created by a millisecond long laser absorption induced micro explosion would travel away from the fibre tip in a time which is much less than the laser pulse period. Unlike the Q-switched NdYAG 1.06 $\mu$m laser, the 1.44 $\mu$m laser is absorbed by water. Absorption by water causes a micro-explosion.

1.06 mm radiation is absorbed very weakly by water so that plasma formation at the fibre tip is necessary to cause a micro explosion. With 1.44 $\mu$m radiation rapid heating and vaporization of water in the vicinity of the fibre tip causes a rapidly expanding vapour bubble. The expansion of this bubble is inhibited by the fibre tip and the surrounding water so that a miniature laser absorption-induced explosion occurs. This explosion is accompanied by a sharp audible click. These laser absorption induced micro explosions have been examined using high speed shadow photography which reveal the shape and velocity of the expansion front of the explosion. These images show a sharp, well-defined front which is similar in appearance to the domed explosion front commonly photographed during nuclear explosions.

In one example, a distal fibre tip was cleaved flat and perpendicular to the fibre axis. Shadow photography did not show a spherically shaped expansion as might be expected, but a highly directional expansion away from the tip in the direction of the fibre axis. The expansion velocity was initially typically 2 millimeters per millisecond and resulted in a bubble typically 5 mm in length and 2 mm in diameter.

In another example a fibre was drawn to a point by heating the fibre with a flame and pulling two parts of the fibre apart. This pointed fibre tip produced very different shadow photographs. A spherical expansion occurred close to the tip of the fibre point and resulted in an approximately spherical bubble of about two to three millimeters diameter.

Continued pulsing of a fiber tip for many thousands of pulses does not apparently influence the formation of absorption induced micro explosions in water. Unlike the Q-switched 1.06 $\mu$m NdYAG laser lithotriptor, damage to the fiber tip surface (which occurs with use and which appears similar to a sand blasting effect) does not influence the creation of micro-explosions in water since the formation of micro-explosions using 1.44 $\mu$m radiation does not rely upon the use of a focusing lens.

It has been discovered that micro-explosions, in water at the tip of a fiberoptic and created by pulsed 1.44 $\mu$m radiation, will erode human stones. If a human stone is immersed in water and the said laser activated fiber tip is brought in contact or near the stone, rapid erosion of the stone surface will occur and fine, powdery, debris will appear in the water. This debris rapidly obscures the stone from view. In contrast, if the stone is placed in air and the said laser activated fiber it is brought near the stone, melting of the stone surface occurs and no erosion is observed. The presence of water around the stone is a necessary means for laser erosion to occur.

If the 1.44 $\mu$m laser-activated fiber tip touches the surface of the stone when high average laser power is applied, a bright flash (associated with plasma formation) may occur. Melting of the fiber tip, melting of the stone and adhesion of the fiber tip to the stone frequently accompany flashing. This undesirable plasma formation is unlike the dye laser lithotriptor (which requires the fiber to touch the stone and cause a flash in order to fragment the stone.) Despite flashing and melting by touching the stone with the fiber tip, it is possible to push the fiber several centimeters through even very hard stone. This is achieved by repeatedly removing the fiber from the small cylindrical hole created by pushing the fiber optic into the stone in order to permit water to enter the hole.

Experiments have been undertaken to find the best distance between the stone surface and the activated fiber tip. In one, fiber was passed through a channel in a cystoscope so that the tip was visible through the lens of the cystoscope—a stone and the fiber tip could be observed simultaneously under water in a rigid container. Small pieces of chalk, (a widely-accepted substitute for soft human calculus,) of known size were fixed by epoxy to the base of the water container. A small wire was attached to the cystoscope to control the distance between the fiber and the chalk. The time required to totally erode a chalk sample was measured as the distance to the chalk was varied. The fiber tip was moved manually across the chalk in a circular pattern which resulted in circular grooves which progressively eroded the chalk. The time required to destroy the chalk sample was used as a measure of erosion rate. Both the pointed and flat fiber tips eroded the chalk most effectively with their tips within two millimeters of the sample. Little improvement in erosion rate resulted from placing the fiber tip closer than 2 millimeters. When the laser was used at low average laser power the best erosion rate occurred when the fiber tip was in contact or close to contact with the stone. The pointed fiber tip generally produced a faster erosion rate than the flat fiber tip. Examination of the interaction of the micro-explosions and a stone was performed with shadow photography. The explosion expansion front from a flat fiber tip strikes the stone surface and tends to be deflected laterally and perpendicular to the direction of the fiber axis. The explosion expansion front from a pointed fiber strikes the stones and tends to be deflected away from the stone along the axis of the fiber. For this reason a greater momentum change of the expansion occurs for a pointed fiber tip which may explain the greater stone erosion rate which results from use of a pointed fiber tip.

Light at 1.44 $\mu$m is absorbed by water within 0.5 mm. Q-switch 1.06 $\mu$m wavelength light from the NdYAG laser and 0.53 $\mu$m wavelength light from the dye laser pass through water essentially unabsorbed. If the direction of the fiberoptic tip is deflected so that light does not strike the stone, the light can pass freely through the surrounding water and strike tissue. In order to avoid accidental injury, the average power from both of these laser lithotriptors is limited to a few watts. This results in slow stone destruction rates for both the Q-switch NdYAG laser lithotriptor and the dye laser lithotriptor.

In order to assess the safety of 1.44 $\mu$m laser lithotripsy, animal experiments were performed. Exposed skin on an anesthetized small animal flank was submerged in water and exposed to the activated fiber tip. In the example of a flat fiber tip, tissue injury was observed only when the axis of the fiber was perpendicular to the skin surface. When the fiber was parallel and in contact with the skin, no injury was observable for an average laser power of 45 watts emerging from the fiber. When the fiber was perpendicular to the skin, injury was observed when the fiber tip was less than 3 mm from the skin with an average laser power of 45 watts. In the example of pointed fiber tip, injury was observed only when the fiber tip was within 1 mm of the skin with an average power of 45 watts. Consequently, for the pointed fiber tip it is necessary to essentially touch tissue to cause accidental injury.

BRIEF DESCRIPTION OF THE DRAWINGS

The drawings illustrate the best mode presently contemplated for carrying out the invention.

DESCRIPTION OF THE PREFERRED EMBODIMENT

Figure 1:
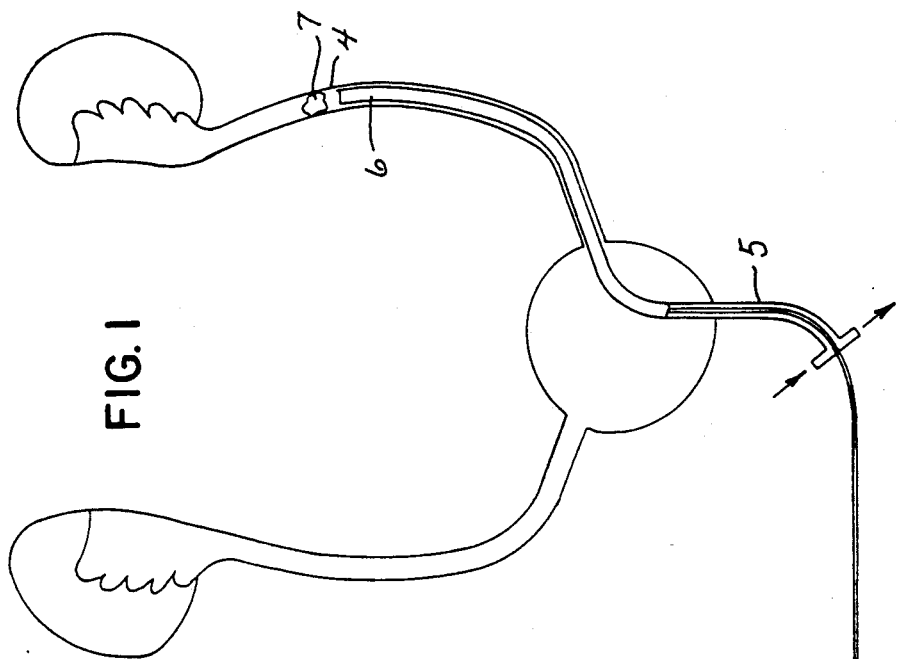
FIG. 1 is a schematic view illustrating the laser lithotriptor constructed and used in accordance with the principles of the present invention.

Referring now to the drawings, FIG. 1 illustrates the laser lithotriptor constructed and used in accordance with this invention. Laser, 1, is adapted to emit radiation which is absorbed by water or water solutions. Although not to limit the generality of the invention, this may be, for example, the $CO_2$ laser operating at the wavelength 10.6 $\mu$m, the NdYAG laser operating at 1.44 $\mu$m, the ErYAG laser operating at 2.9 $\mu$m, the $T_m H_o C_r YAG$ laser operating at 2.16 $\mu$m, the HF laser operating at 2.9 $\mu$m or the $C_o M_g F_2$ laser operating at 1.9 $\mu$m. As a specific example, the laser 1 may be an NdYAG laser adapted to emit radiation at 1.44 $\mu$m and to emit light pulses with energy adjustable from zero to 2 Joules, pulse width adjustable from 0.1 to 100 milliseconds, pulse repetition rate adjustable from 0 to 100 pulses per second and average laser power emission adjustable from 0 to 50 watts.

Pulsed pumping source 2 drives the laser 1 so as to produce repetitive pulses of light from the laser. For examples, this may be the electrical excitation means for the lamps of the NdYAG laser or it may be the electrical excitation means for the $CO_2$ laser discharge. Other means of pulsing the laser are anticipated. For example, an electrical or mechanical shutter within the laser resonator will result in pulsed laser emission known in the art as Q-switching. As a specific example, pumping source 2 may be a switched current source which drives the laser pumping lamps of an NdYAG laser adapted to operate at 1.44 $\mu$m. The pulse duration varies from nearly zero to 100 milliseconds and the pulse repetition rate varies from one 1 to 100 pulses per second.

Light delivery means 3 transmits the laser light from the laser into the human body to the proximity of a stone. The delivery means may be a fiberoptic, it may be a rigid light guide or it may be a flexible light waveguide. As a specific example, this may be a 600 $\mu$m quartz core fiberoptic manufactured to have low water content. This is known in the art as anhydrous quartz fiberoptic.

The body part, 4, illustrated is the ureter. This may be the bladder the urethera, the cervix of the kidney, the gall bladder or the common bile duct. This is not to limit the generality of the invention since calcification occurs in other body parts such as blood vessels.

Irrigation means, 5 carries water or a water solution to the vicinity of the stone. This means of ensuring that the fiber tip and the stone are immersed in water also serves to remove the powder-like debris from the body. It may be plastic or metal tubing or it may be liquid-conducting channels in a rigid or a flexible endoscope. As a specific example, irrigation means 5 may be the irrigation channel of a resectoscope which has been modified to pass a fiberoptic.

Figure 2:
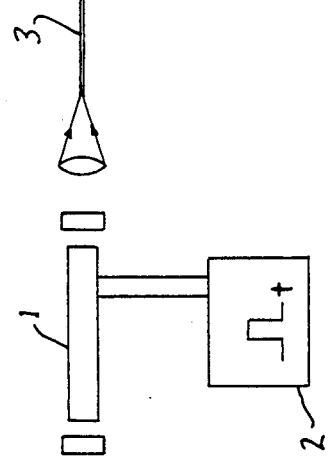
FIG. 2 illustrates the juxtaposition of the fiber tip and the stone.
Figure 2:
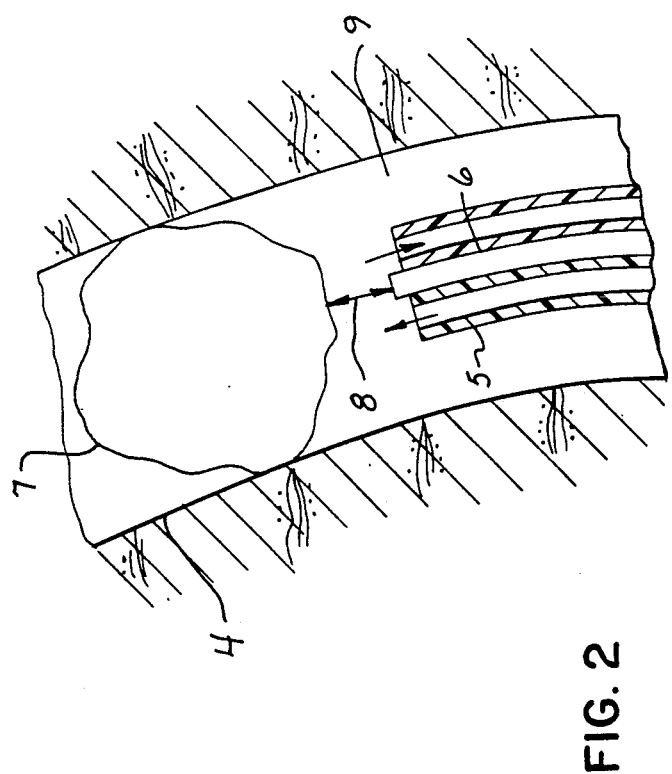

Referring now to FIG. 2, this illustrates the juxtaposition of the laser fiberoptic and the human stone.

The fiber tip, 6, may be the flat end of a fiberoptic or it may be the pointed or rounded tip of a fiberoptic. It may also be the output window for a hollow light guide or a flexible waveguide. It may also be the pointed or flat attachement made for a transparent hard material such as sapphire.

The stone, 7, may be any form of human concrement such as soft cholesterol gall stone or hard calcium oxalate urinary stones. The stone, 7, is disposed closely to the fiber tip, 6, for maximum lithotriptic effect.

As a specific example the distance, 8, between the stone and fiber tip is 2 mm. The immersing liquid, 9, covers the fiber tip and the stone and in particular fills the space, 8, between them. This liquid should be light-absorbing. It may be water or a water containing solution or it may be a light-absorbing solution.

When used as a lithotriptor the preferred geometry is NdYAG laser operating at 1.44 $\mu$m which emits 27 pulses per second with a pulse energy of 1.5 Joules. This laser is coupled to the stone through a 600 $\mu$m core anhydrous quartz fiberoptic. The fiber tip is held within 2 mm of the stone surface and is pointed. Both the fiber tip and the stone are immersed and irrigated with water.

Various modes of carrying out the invention are contemplated.

I claim:

1. A method of destroying a concrement in the human body, the method comprising:
   supplying a liquid to the vicinity of a concrement located in a human body, the liquid being capable of absorbing laser light having a chosen frequency;
   placing one tip end of a light transmission means closely adjacent and directed towards the concrement, whereby a gap is left between the tip end of the light transmission means and the concrement, the liquid filling the gap; and
   applying to the light transmission means laser light pulses having the chosen frequency to create laser absorption induced micro-explosions in the liquid, whereby the concrement is eroded and produces debris.

2. The method of claim 1 further including removing the liquid and the debris from the vicinity of the stone.

3. The method of claim 2 in which the tip end of the light transmission means is placed within 2 mm of the concrement.

4. The method of claim 2 in which the liquid contains water, and the frequency is a frequency that is absorbable by water.

5. The method of claim 4 in which the laser light is generated by a 1.44 $\mu$m NdYAG laser.

* * * * *